(12) United States Patent
Warren et al.

(10) Patent No.: US 7,392,085 B2
(45) Date of Patent: Jun. 24, 2008

(54) MULTIPLE ELECTRODE VECTORS FOR IMPLANTABLE CARDIAC TREATMENT DEVICES

(75) Inventors: Jay A. Warren, San Juan Capistrano, CA (US); Gust H. Bardy, Seattle, WA (US)

(73) Assignee: Cameron Health, Inc., San Clemente, CA (US)

( * ) Notice: Subject to any disclaimer, the term of this patent is extended or adjusted under 35 U.S.C. 154(b) by 636 days.

(21) Appl. No.: 10/901,258

(22) Filed: Jul. 27, 2004

(65) Prior Publication Data

US 2005/0049644 A1   Mar. 3, 2005

Related U.S. Application Data

(63) Continuation-in-part of application No. 10/856,084, filed on May 7, 2004, now Pat. No. 7,330,757, application No. 10/901,258, which is a continuation-in-part of application No. 10/863,599, filed on Jun. 8, 2004, which is a continuation of application No. 09/990,510, filed on Nov. 21, 2001, now Pat. No. 6,754,528, application No. 10/901,258, which is a continuation-in-part of application No. 10/858,598, filed on Jun. 1, 2004, now Pat. No. 7,248,921.

(60) Provisional application No. 60/490,779, filed on Jul. 28, 2003, provisional application No. 60/475,279, filed on Jun. 2, 2003, provisional application No. 60/474,323, filed on May 29, 2003.

(51) Int. Cl.
*A61N 1/00* (2006.01)
(52) U.S. Cl. .......................................... 607/27
(58) Field of Classification Search ............. 607/9–28
See application file for complete search history.

(56) References Cited

U.S. PATENT DOCUMENTS 3,653,387 A    4/1972   Ceier (Continued)

FOREIGN PATENT DOCUMENTS

DE    298 01 807 U1    7/1998

(Continued)

OTHER PUBLICATIONS

U.S. Appl. No. 10/856,084, filed May 27, 2004, Ostroff et al.

(Continued)

*Primary Examiner*—Scott M Getzow
(74) *Attorney, Agent, or Firm*—Pramudji Wendt & Tran, LLP; Ari Pramudji

(57) ABSTRACT

The implantable cardiac treatment system of the present invention is capable of choosing the most appropriate electrode vector to sense within a particular patient. In certain embodiments, the implantable cardiac treatment system determines the most appropriate electrode vector for continuous sensing based on which electrode vector results in the greatest signal amplitude, or some other useful metric such as signal-to-noise ratio (SNR). The electrode vector possessing the highest quality as measured using the metric is then set as the default electrode vector for sensing. Additionally, in certain embodiments of the present invention, a next alternative electrode vector is selected based on being generally orthogonal to the default electrode vector. In yet other embodiments of the present invention, the next alternative electrode vector is selected based on possessing the next highest quality metric after the default electrode vector. In some embodiments, if analysis of the default vector is ambiguous, the next alternative electrode vector is analyzed to reduce ambiguity.

22 Claims, 8 Drawing Sheets

U.S. PATENT DOCUMENTS

| | | |
|---|---|---|
| 3,710,374 A | 1/1973 | Kelly |
| 3,911,925 A | 10/1975 | Tillery, Jr. |
| 4,030,509 A | 6/1977 | Heilman et al. |
| 4,157,720 A | 6/1979 | Greatbatch |
| 4,164,946 A | 8/1979 | Langer |
| 4,184,493 A | 1/1980 | Langer et al. |
| 4,191,942 A | 3/1980 | Long |
| 4,210,149 A | 7/1980 | Heilman et al. |
| RE30,387 E | 8/1980 | Denniston, III et al. |
| 4,223,678 A | 9/1980 | Langer et al. |
| 4,248,237 A | 2/1981 | Kenny |
| 4,254,775 A | 3/1981 | Langer |
| 4,291,707 A | 9/1981 | Heilman et al. |
| 4,300,567 A | 11/1981 | Kolenik et al. |
| 4,314,095 A | 2/1982 | Moore et al. |
| 4,375,817 A | 3/1983 | Engle et al. |
| 4,402,322 A | 9/1983 | Duggan |
| 4,407,288 A | 10/1983 | Langer et al. |
| 4,424,818 A | 1/1984 | Doring et al. |
| 4,450,527 A | 5/1984 | Sramek |
| 4,548,209 A | 10/1985 | Weilders et al. |
| 4,567,900 A | 2/1986 | Moore |
| 4,595,009 A | 6/1986 | Leinders |
| 4,602,637 A | 7/1986 | Elmqvist et al. |
| 4,603,705 A | 8/1986 | Speicher et al. |
| 4,693,253 A | 9/1987 | Adams |
| 4,727,877 A | 3/1988 | Kallok |
| 4,750,494 A | 6/1988 | King |
| 4,765,341 A | 8/1988 | Mower et al. |
| 4,768,512 A | 9/1988 | Imran |
| 4,800,883 A | 1/1989 | Winstrom |
| 4,830,005 A | 5/1989 | Woskow |
| 4,944,300 A | 7/1990 | Saksena |
| 5,044,374 A | 9/1991 | Lindemans et al. |
| 5,105,810 A | 4/1992 | Collins et al. |
| 5,105,826 A | 4/1992 | Smits et al. |
| 5,109,842 A | 5/1992 | Adinolfi |
| 5,129,392 A | 7/1992 | Bardy et al. |
| 5,133,353 A | 7/1992 | Hauser |
| 5,144,946 A | 9/1992 | Weinberg et al. |
| 5,184,616 A | 2/1993 | Weiss |
| 5,191,901 A | 3/1993 | Dahl et al. |
| 5,203,348 A | 4/1993 | Dahl et al. |
| 5,215,081 A | 6/1993 | Ostroff |
| 5,230,337 A | 7/1993 | Dahl et al. |
| 5,255,692 A | 10/1993 | Neubauer et al. |
| 5,261,400 A | 11/1993 | Bardy |
| 5,271,411 A | 12/1993 | Ripley et al. |
| 5,300,106 A | 4/1994 | Dahl et al. |
| 5,313,953 A | 5/1994 | Yomtov et al. |
| 5,331,966 A | 7/1994 | Bennett et al. |
| 5,342,407 A | 8/1994 | Dahl et al. |
| 5,366,496 A | 11/1994 | Dahl et al. |
| 5,376,103 A | 12/1994 | Anderson et al. |
| 5,376,104 A | 12/1994 | Sakai et al. |
| 5,385,574 A | 1/1995 | Hauser et al. |
| 5,391,200 A | 2/1995 | KenKnight et al. |
| 5,405,363 A | 4/1995 | Kroll et al. |
| 5,411,539 A | 5/1995 | Neisz |
| 5,411,547 A | 5/1995 | Causey, III |
| 5,413,591 A | 5/1995 | Knoll |
| 5,423,326 A | 6/1995 | Wang et al. |
| 5,431,693 A | 7/1995 | Schroeppel |
| 5,439,485 A | 8/1995 | Mar et al. |
| 5,447,521 A | 9/1995 | Anderson et al. |
| 5,476,503 A | 12/1995 | Yang |
| 5,486,199 A | 1/1996 | Kim et al. |
| 5,501,702 A | 3/1996 | Plicchi et al. |
| 5,509,923 A | 4/1996 | Middleman et al. |
| 5,509,928 A | 4/1996 | Acken |
| 5,522,852 A | 6/1996 | White et al. |
| 5,531,765 A | 7/1996 | Pless |
| 5,531,766 A | 7/1996 | Kroll et al. |
| 5,534,019 A | 7/1996 | Paspa |
| 5,534,022 A | 7/1996 | Hoffmann et al. |
| 5,558,098 A | 9/1996 | Fain |
| 5,597,956 A | 1/1997 | Ito et al. |
| 5,601,607 A | 2/1997 | Adams |
| 5,603,732 A | 2/1997 | Dahl et al. |
| 5,607,455 A | 3/1997 | Armstrong |
| 5,618,287 A | 4/1997 | Fogarty et al. |
| 5,620,477 A | 4/1997 | Pless et al. |
| 5,643,328 A | 7/1997 | Cooke et al. |
| 5,645,586 A | 7/1997 | Meltzer |
| 5,658,317 A | 8/1997 | Haefner et al. |
| 5,658,319 A | 8/1997 | Kroll |
| 5,658,321 A | 8/1997 | Fayram et al. |
| 5,674,260 A | 10/1997 | Weinberg |
| 5,690,648 A | 11/1997 | Fogarty et al. |
| 5,690,683 A | 11/1997 | Haefner et al. |
| 5,697,953 A | 12/1997 | Kroll et al. |
| 5,713,926 A | 2/1998 | Hauser et al. |
| 5,766,226 A | 6/1998 | Pedersen |
| 5,776,169 A | 7/1998 | Schroeppel |
| 5,814,090 A | 9/1998 | Latterell et al. |
| 5,827,197 A | 10/1998 | Bocek et al. |
| 5,827,326 A | 10/1998 | Kroll et al. |
| 5,836,976 A | 11/1998 | Min et al. |
| 5,843,132 A | 12/1998 | Ilvento |
| 5,895,414 A | 4/1999 | Sanchez-Zambrano |
| 5,904,705 A | 5/1999 | Kroll et al. |
| 5,919,211 A | 7/1999 | Adams |
| 5,919,222 A | 7/1999 | Hjelle et al. |
| 5,925,069 A | 7/1999 | Graves et al. |
| 5,935,154 A | 8/1999 | Westlund |
| 5,941,904 A | 8/1999 | Johnston et al. |
| 5,957,956 A | 9/1999 | Kroll et al. |
| 5,991,657 A | 11/1999 | Kim |
| 5,999,853 A | 12/1999 | Stoop et al. |
| 6,014,586 A | 1/2000 | Weinberg et al. |
| 6,026,325 A | 2/2000 | Weinberg et al. |
| 6,041,251 A | 3/2000 | Kim et al. |
| 6,047,210 A | 4/2000 | Kim et al. |
| 6,052,617 A | 4/2000 | Kim |
| 6,058,328 A | 5/2000 | Levine et al. |
| 6,093,173 A | 7/2000 | Balceta et al. |
| 6,095,987 A | 8/2000 | Shmulewitz et al. |
| H1905 H | 10/2000 | Hill |
| 6,128,531 A | 10/2000 | Campbell-Smith |
| 6,144,866 A | 11/2000 | Miesel et al. |
| 6,144,879 A | 11/2000 | Gray |
| 6,148,230 A | 11/2000 | KenKnight |
| 6,185,450 B1 | 2/2001 | Seguine et al. |
| 6,266,554 B1 | 7/2001 | Hsu et al. |
| 6,266,567 B1 | 7/2001 | Ishikawa et al. |
| 6,278,894 B1 | 8/2001 | Salo et al. |
| 6,280,462 B1 | 8/2001 | Hauser et al. |
| 6,308,095 B1 | 10/2001 | Hsu et al. |
| 6,334,071 B1 | 12/2001 | Lu |
| 6,345,198 B1 | 2/2002 | Mouchawar et al. |
| 6,377,844 B1 | 4/2002 | Graen |
| 6,381,493 B1 * | 4/2002 | Stadler et al. .................. 607/9 |
| 6,411,844 B1 | 6/2002 | Kroll et al. |
| 6,493,579 B1 | 12/2002 | Gilkerson et al. |
| 6,493,584 B1 | 12/2002 | Lu |
| 6,516,225 B1 | 2/2003 | Florio |
| 6,567,691 B1 | 5/2003 | Stadler |
| 6,574,505 B1 | 6/2003 | Warren |
| 6,625,490 B1 | 9/2003 | McClure et al. |
| 6,647,292 B1 | 11/2003 | Bardy et al. |
| 6,684,100 B1 | 1/2004 | Sweeney et al. |
| 6,687,540 B2 | 2/2004 | Marcovecchio |
| 6,699,200 B2 | 3/2004 | Cao et al. |
| 6,708,058 B2 | 3/2004 | Kim et al. |

| | | | |
|---|---|---|---|
| 6,708,062 B2 | 3/2004 | Ericksen et al. |
| 6,721,597 B1 | 4/2004 | Bardy et al. |
| 6,728,572 B2 | 4/2004 | Hsu et al. |
| 6,731,978 B2 | 5/2004 | Olson et al. |
| 6,754,528 B2 | 6/2004 | Bardy et al. |
| 6,778,860 B2 | 8/2004 | Ostroff et al. |
| 6,788,974 B2 | 9/2004 | Bardy et al. |
| 6,889,079 B2 | 5/2005 | Bocek et al. |
| 6,909,916 B2 | 6/2005 | Spinelli et al. |
| 6,959,212 B2 | 10/2005 | Hsu et al. |
| 7,016,730 B2 | 3/2006 | Ternes |
| 7,020,523 B1 | 3/2006 | Lu et al. |
| 7,027,862 B2 | 4/2006 | Dahl et al. |
| 7,031,764 B2 | 4/2006 | Schwartz et al. |
| 7,085,599 B2 | 8/2006 | Kim et al. |
| 7,162,301 B2 | 1/2007 | Kim et al. |
| 7,167,747 B2 | 1/2007 | Gunderson et al. |
| 7,184,818 B2 | 2/2007 | Kim et al. |
| 7,191,004 B2 | 3/2007 | Kim et al. |
| 7,266,409 B2 | 9/2007 | Gunderson |
| 2001/0027330 A1 | 10/2001 | Sullivan et al. |
| 2001/0034487 A1 | 10/2001 | Cao et al. |
| 2004/0215240 A1 | 10/2004 | Lovett et al. |
| 2004/0230229 A1 | 11/2004 | Lovett et al. |
| 2004/0230243 A1 | 11/2004 | Haefner et al. |
| 2005/0004615 A1 | 1/2005 | Sanders |
| 2005/0203581 A1 | 9/2005 | Spinelli et al. |
| 2005/0245976 A1 | 11/2005 | Wang |
| 2006/0052830 A1 | 3/2006 | Spinelli et al. |
| 2006/0116730 A1 | 6/2006 | Gunderson |
| 2006/0161205 A1 | 7/2006 | Mitrani et al. |
| 2006/0167502 A1 | 7/2006 | Haefner |
| 2007/0233196 A1 | 10/2007 | Stadler et al. |
| 2007/0239220 A1 | 10/2007 | Greenhut et al. |

FOREIGN PATENT DOCUMENTS

| | | | |
|---|---|---|---|
| EP | 0 095 727 A1 | 12/1983 |
| EP | 0 316 616 A2 | 5/1989 |
| EP | 0 316 616 A3 | 5/1989 |
| EP | 0 347 353 A1 | 12/1989 |
| EP | 0 517 494 A3 | 12/1992 |
| EP | 0 517 494 B1 | 12/1992 |
| EP | 0 518 599 A2 | 12/1992 |
| EP | 0 518 599 B1 | 12/1992 |
| EP | 0 536 873 B1 | 4/1993 |
| EP | 0 586 858 B1 | 3/1994 |
| EP | 0 627 237 A1 | 12/1994 |
| EP | 0 641 573 A2 | 3/1995 |
| EP | 0 641 573 A3 | 3/1995 |
| EP | 0 677 301 A1 | 10/1995 |
| EP | 0 813 889 A2 | 12/1997 |
| EP | 0 917 887 A1 | 5/1999 |
| EP | 0 923 130 A1 | 6/1999 |
| WO | WO 93/19809 A1 | 10/1993 |
| WO | WO 97/29802 A2 | 8/1997 |
| WO | WO 98/25349 A1 | 6/1998 |
| WO | WO 99/03534 A1 | 1/1999 |
| WO | WO 99/37362 A1 | 7/1999 |
| WO | WO/99/48554 A1 | 9/1999 |
| WO | WO 99/53991 A1 | 10/1999 |
| WO | 1 000 634 A1 | 5/2000 |
| WO | WO 00/41766 A1 | 7/2000 |
| WO | WO 00/50120 A1 | 8/2000 |
| WO | WO 01/43649 A1 | 6/2001 |
| WO | WO 01/56166 A2 | 8/2001 |
| WO | WO 02/22208 A2 | 3/2002 |
| WO | WO 02/22208 A3 | 3/2002 |
| WO | WO 02/24275 A2 | 3/2002 |
| WO | WO 02/24275 A3 | 3/2002 |
| WO | WO 02/068046 A1 | 9/2002 |
| WO | WO 03/018121 A2 | 3/2003 |
| WO | WO 03/020367 A1 | 3/2003 |
| WO | WO/03/065613 A1 | 8/2003 |
| WO | WO 2004/091720 A2 | 10/2004 |
| WO | WO/2007/140207 A1 | 12/2007 |
| WO | WO/2007/140214 A1 | 12/2007 |

OTHER PUBLICATIONS

U.S. Appl. No. 10/858,598, filed Jun. 1, 2004, Palreddy et al.
U.S. Appl. No. 10/863,599, filed Jun. 8, 2004, Bardy et al.
Bardy, Gust H. et al., "Multicenter Experience with a Pectoral Unipolar Implantable Cardioverter-Defibrillator," *JACC*, Aug. 1996, vol. 28, No. 2, pp. 400-410.
Friedman, Richard A. et al., "Implantable Defibrillators In Children: From Whence to Shock," *Journal of Cardiovascular Electrophysiology*, vol. 12, No. 3, Mar. 2001, pp. 361-362.
Ge, Dingfei et al., "Cardiac Arrhythmia Classification Using Autoregressive Modeling," *BioMedical Engineering OnLine*, http://www.biomedical-engineering-online.com, Nov. 13, 2002, 12 pages.
Gradaus, Rainer et al., "Nonthoracotomy Implantable Cardioverter Defibrillator Placement in Children: Use of Subcutaneous Array Leads and Abdominally Placed Implantable Cardioverter Defibrillators in Children," *Journal of Cardiovascular Electrophysiology*, vol. 12, No. 3, Mar. 2001, pp. 356-360.
Higgins, Steven L. et al., "The First Year Experience with the Dual Chamber ICD," *PACE*, Jan. 2000, vol. 23, pp. 18-25.
Mirowski, M. et al., "Automatic Detection and Defibrillation of Lethal Arrhythmias-A New Concept," *JAMA*, vol. 213, No. 4, Jul. 27, 1970, pp. 615-616.
Olson, Walter H. et al., "Onset and Stability for Ventricular Tachyarrhythmia Detection in an Implantable Pacer-Cardioverter-Defibrillator," *IEEE*, (1987) pp. 167-170.
Schuder, John C., "Completely Implanted Defibrillator," *JAMA*, vol. 214, No. 6, Nov. 9, 1970. p. 1123 (single sheet).
Schuder, John C. et al., "Experimental Ventricular Defibrillation with an Automatic and Completely Implanted System," *Trans. Amer. Soc. Artif. Int. Organs*, vol. XVI (1970) pp. 207-212.
Schuder, John C., "The Role of an Engineering Oriented Medical Research Group in Developing Improved Methods and Devices for Achieving Ventricular Defibrillation: The University of Missouri Experience," *PACE*, vol. 16, Jan. 1993, pp. 95-124.
Schuder, John C. et al., "Standby Implanted Defibrillators," *Arch Intern. Med*, vol. 127, Feb. 1971, p. 317 (single sheet).
Schuder, John C. et al., "Transthoracic Ventricular Defibrillation in the Dog with Truncated and Untruncated Exponential Stimuli," *IEEE Transactions on Bio-Medical Engineering*, vol. BME-18, No. 6, Nov. 1971, pp. 410-415.
Schwacke, H. et al., "Komplikationen mit Sonden bei 340 Patienten mit einem Implantierbaren Kardioverter/Defibrillator," *Z Kardiol* (1999) vol. 88, No. 8, pp. 559-565.
Tietze U. et al., "Halbleiter-Schaltungstechnik,"© Springer-Verlag (Berlin, Germany), (1991), pp. 784-786.
Valenzuela, Terrence D. et al., "Outcomes of Rapid Defibrillation by Security Officers After Cardiac Arrest in Casinos," *The New England Journal of Medicine*, Oct. 26, 2000, vol. 343, No. 17, pp. 1206-1209.
Walters, R.A. et al., "Analog to Digital Conversion Techniques in Implantable Devices," *Annual International Conference of the IEEE Engineering in Medicine and Biology Society*, vol. 13 No. 4 (1991) p. 1674-1676.
U.S. Appl. No. 60/786,981, filed Mar. 29, 2006, Stadler et al.
U.S. Appl. No. 60/632,000, filed Dec. 1, 2004, Gunderson.
U.S. Appl. No. 60/186,235, filed Mar. 1, 2000, Cao et al.

* cited by examiner

MULTIPLE ELECTRODE VECTORS FOR IMPLANTABLE CARDIAC TREATMENT DEVICES

REFERENCE TO RELATED APPLICATIONS

The present application claims the benefit of U.S. Provisional Application Ser. No. 60/490,779, filed Jul. 28, 2003, entitled MULTIPLE ELECTRODE VECTORS IN A SUBCUTANEOUS ICD. This application is also a continuation-in-part of U.S. patent application Ser. No. 10/856,084 filed May 27, 2004 now U.S. Pat. No. 7,330,757, entitled METHOD FOR DISCRIMINATING BETWEEN VENTRICULAR AND SUPRAVENTRICULAR ARRHYTHMIAS, which claims the benefit of U.S. Provisional Application Ser. No. 60/474,323, filed May 29, 2003. This application is also a continuation-in-part of co-pending U.S. application Ser. No. 10/863,599, filed Jun. 8, 2004, entitled APPARATUS AND METHOD OF ARRHYTHMIA DETECTION IN A SUBCUTANEOUS IMPLANTABLE CARDIOVERTER/DEFIBRILLATOR, which is a continuation of U.S. application Ser. No. 09/990,510, filed Nov. 21, 2001, entitled APPARATUS AND METHOD OF ARRHYTHMIA DETECTION IN A SUBCUTANEOUS IMPLANTABLE CARDIOVERTER/DEFIBRILLATOR, now U.S. Pat. No. 6,754,528. This application is also a continuation-in-part of U.S. patent application Ser. No. 10/858,598 filed Jun. 1, 2004, entitled METHOD AND DEVICES FOR PERFORMING CARDIAC WAVEFORM APPRAISAL, now U.S. Pat. No. 7,248,921, which claims the benefit of U.S. Provisional Application Ser. No. 60/475,279, filed Jun. 2, 2003. The disclosure of each of these applications is incorporated herein by reference.

FIELD OF THE INVENTION

The present invention relates generally to methods and devices for improving sensing in an implantable cardiac treatment system. More particularly, the present invention relates to the placement of electrodes in an implantable pacing or cardioversion/defibrillation system at defined locations within a patient to create multiple electrode vectors for improved far-field sensing and improved sensing of cardiac events.

BACKGROUND

Implantable cardiac rhythm management devices are an effective treatment in managing irregular cardiac rhythms in particular patients. Implantable cardiac rhythm management devices are capable of recognizing and treating arrhythmias with a variety of therapies. These therapies include anti-bradycardia pacing for treating bradycardia, anti-tachycardia pacing or cardioversion pulsing for treating ventricular tachycardia, and high energy shocking for treating ventricular fibrillation. Usually, the cardiac rhythm management device delivers these therapies for the treatment of tachycardia in sequence starting with anti-tachycardia pacing and then proceeding to low energy shocks, and then finally to high energy shocks. Sometimes, however, only one of these therapies is selected depending upon the tachyarrhythmia detected.

To effectively deliver treatment, cardiac rhythm management devices must first accurately detect and classify a cardiac event. Through the accurate classification of cardiac events, these cardiac rhythm management devices are able to classify the type of arrhythmia that is occurring (if any) and assess the appropriate therapy to provide to the heart (if indicated). A problem arises, however, when the cardiac rhythm management device misclassifies an event and, as a result, delivers inappropriate therapy or fails to deliver therapy.

Besides being physically painful to the patient, when a cardiac rhythm management device delivers inappropriate treatment, it can be extremely disconcerting. Moreover, delivery of an inappropriate therapy can intensify the malignancy of the cardiac arrhythmia or cause an arrhythmia where one was not present. The accuracy of a sensing architecture is, therefore, an important factor in ensuring that appropriate therapy is delivered to a patient.

SUMMARY

In a first embodiment, an implantable cardiac treatment system is provided with electrodes disposed at several locations in a patient's thorax. During operation of the system, various sensing vectors can be periodically, repeatedly, or continuously monitored to select the best sensing vector for event detection and classification. A sensing vector may be selected and then used for analysis. In another embodiment, multiple vectors may be simultaneously analyzed to provide a tiered or prioritized detection scheme, or to provide a secondary check on a higher priority vector. For example, a first vector may be used as the higher priority vector, and a second vector may be used to verify that sensed with the first vector. Alternatively, ambiguity may be reduced by the use of a second vector to check on a first vector. Additional embodiments include implantable cardiac treatment systems and operational circuitry for use in implantable cardiac treatment systems which are adapted for performing these methods. Some embodiments take the form of subcutaneous implantable cardiac treatment systems.

DETAILED DESCRIPTION

The following detailed description should be read with reference to the Figures, in which like elements in different Figures are numbered identically. The Figures, which are not necessarily to scale, depict selected embodiments and are not intended to limit the scope of the invention. Those skilled in the art will recognize that many of the examples and elements of the examples have suitable alternatives that may be utilized.

The present invention is generally related to cardiac rhythm management devices (e.g., an Implantable Cardioverter/Defibrillator (ICD) system) that provide therapy for patients experiencing particular arrhythmias. The present invention is directed toward sensing architectures for use in cardiac rhythm management devices. In particular, the present invention is suited for ICD systems capable of detecting and defibrillating harmful arrhythmias. Although the sensing architecture is intended primarily for use in an implantable medical device that provides defibrillation therapy, the invention is also applicable to cardiac rhythm management devices directed toward anti-tachyarrhythmia pacing (ATP) therapy, pacing, and other cardiac rhythm devices capable of performing a combination of therapies to treat rhythm disorders, including external devices.

Figure 1A:
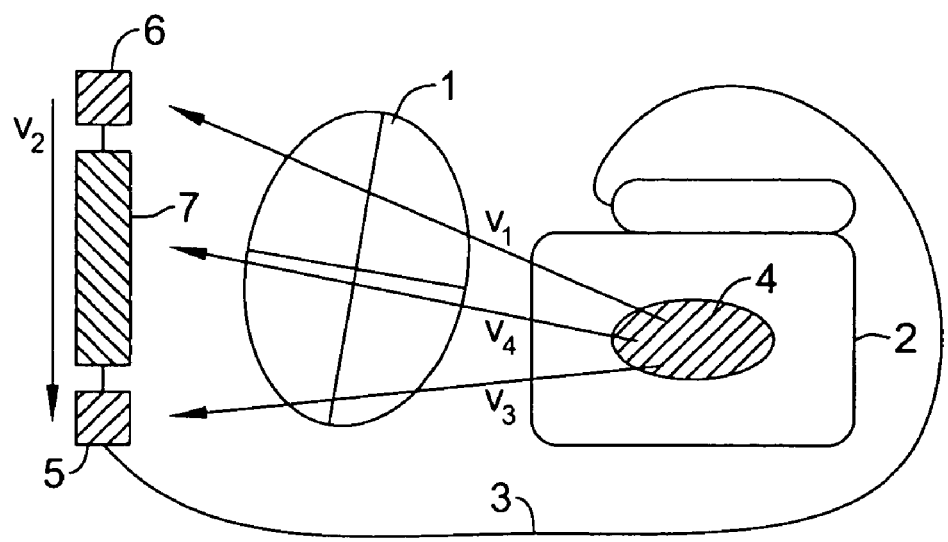
FIGS. 1A-1B illustrate, respectively, representative subcutaneous and intravenous implantable cardiac treatment systems.
Figure 1B:
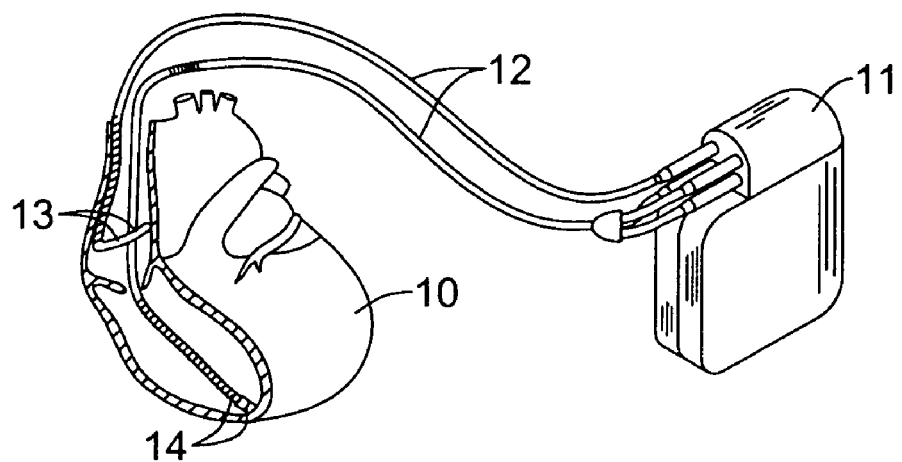

To date, ICD systems have been epicardial systems or transvenous systems implanted generally as shown in FIG. 1B, however, as further explained herein, the present invention is also adapted to function with a subcutaneous ICD system as shown in FIG. 1A.

FIG. 1A illustrates a subcutaneously placed ICD system. In this illustrative embodiment, the heart 1 is monitored using a canister 2 coupled to a lead system 3. The canister 2 may include an electrode 4 thereon, while the lead system 3 connects to sensing electrodes 5, 6, and a coil electrode 7 that may serve as a shock or stimulus delivery electrode as well as a sensing electrode. The general path between various electrodes define a number of sensing vectors V1, V2, V3, V4. It can be seen that each vector provides a different vector "view" of electrical activity in the heart 1. The system may be implanted subcutaneously as illustrated, for example, in U.S. Pat. Nos. 6,647,292 and 6,721,597, the disclosures of which are both incorporated herein by reference. By subcutaneous placement, it is meant that sensing and therapy can be accomplished with electrode placement that does not require insertion of an electrode into a heart chamber, the heart muscle, or the patient's vasculature.

FIG. 1B illustrates a transvenous ICD system. The heart 10 is monitored and treated by a system including a canister 11 coupled to a lead system 12 including atrial electrodes 13 and ventricular electrodes 14. A number of configurations for the electrodes may be used, including placement within the heart, adherence to the heart, or disposition within the patient's vasculature. For example, Olson et al., in U.S. Pat. No. 6,731,978, illustrate electrodes disposed in each chamber of the heart for sensing, as well as shocking electrodes in addition to the sensing electrodes.

The present invention, in some embodiments, is also embodied by operational circuitry including select electrical components provided within the canister 2 (FIG. 1A) or canister 11 (FIG. 1B). In such embodiments, the operational circuitry may be configured to enable the methods to be performed. In some similar embodiments, the present invention may be embodied in readable instruction sets such as a program encoded in machine or controller readable media, wherein the readable instruction sets are provided to enable the operational circuitry to perform the analysis discussed herein in association with various embodiments. Further embodiments may include a controller or microcontroller adapted to read and execute embodiments discussed herein.

In the system illustrated in FIG. 1A, the subcutaneous implantable cardiac treatment device can sense a plurality of electrode vectors. In particular, the configuration depicted can sense at least between the first sensing electrode 6 and the canister or housing electrode 4. The canister or housing electrode 4 can be a part of the housing or canister, the housing or canister itself may be an electrode 4, or alternatively, the electrode can be attached to or on the housing. This sensing relationship forms electrode vector $v_1$. The device can further sense between the first sensing electrode 6 and the second sensing electrode 5 to form electrode vector $v_2$. A third sensing configuration is created by sensing between the second sensing electrode 5 and the canister electrode 4. This sensing relationship forms electrode vector $v_3$. The last illustrated electrode vector is between the shocking electrode 7 and the canister electrode 4 forming electrode vector $v_4$. The system depicted in FIG. 1a is illustrative only. The purpose of the figure is to demonstrate some of the possible electrode vectors that can be formed with implantable cardioverter-defibrillator systems, particularly with subcutaneous systems. Other electrode arrangements and electrode types may be utilized without deviating from the spirit and scope of the invention.

Figure 2:
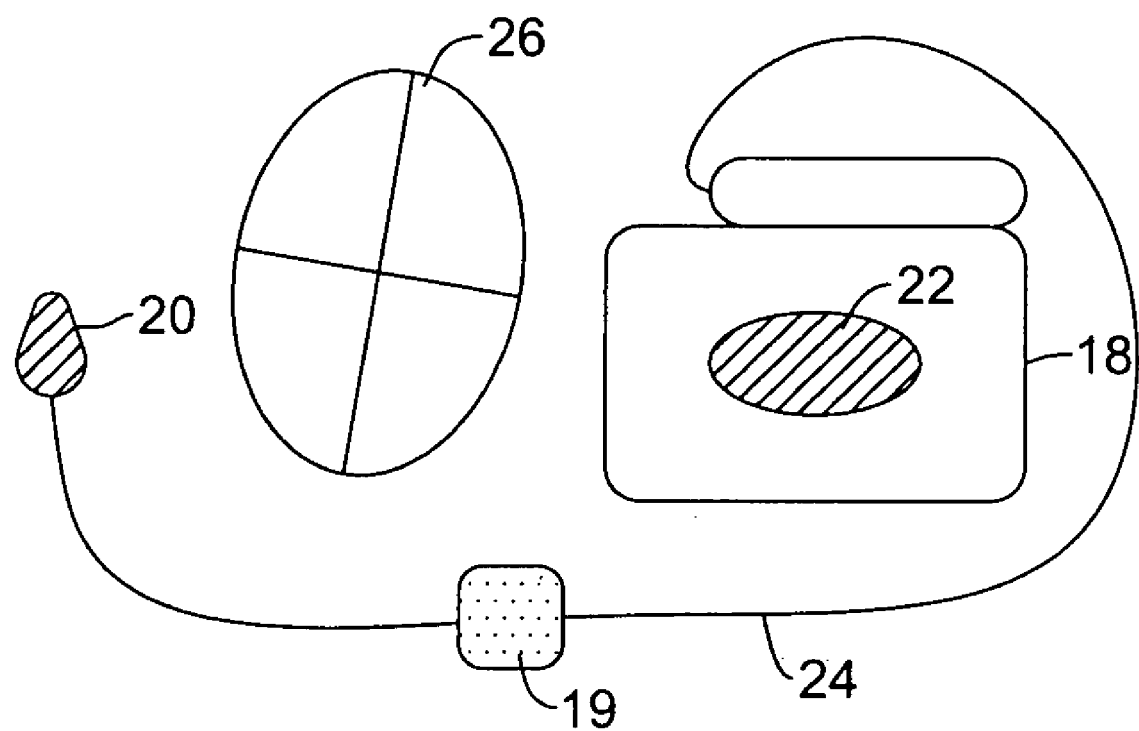
FIG. 2 shows a subcutaneous implantable cardiac treatment system having an alternative subcutaneous electrode system arrangement.

An alternative subcutaneous embodiment is depicted in FIG. 2. A canister 18 is electrically coupled to electrodes 19, 20, 22, with electrodes 19, 20 disposed on a lead 24 and electrode 22 disposed on the canister 18. The several electrodes 19, 20, 22 provide various sensing vectors around heart 26. The illustrative leads and electrodes may have various lengths. As further discussed below, certain sizes and lengths may provide advantageous sensing characteristics.

Figure 3A:
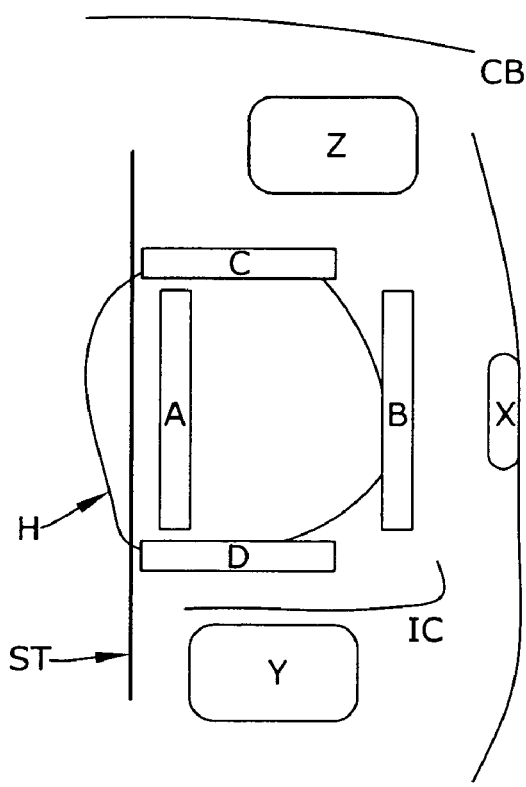
FIGS. 3A and 3B show three positions for the placement of an implantable cardiac treatment device and four subcutaneous positions for the placement of an electrode.
Figure 3B:
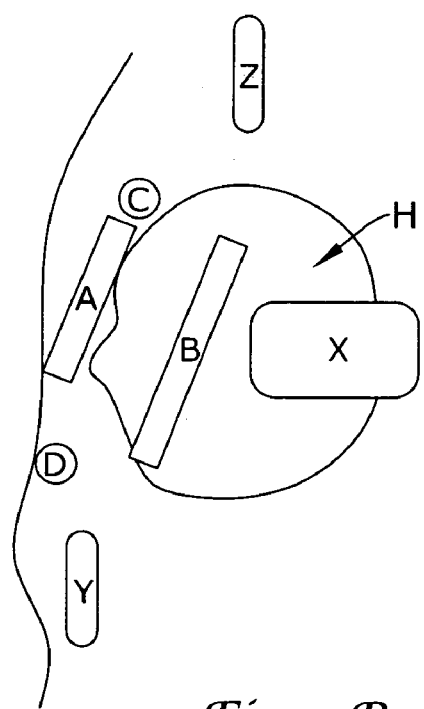

FIGS. 3A and 3B show three illustrative subcutaneous positions (X, Y and Z) for the placement of an ICD in a patient's thoracic region. FIG. 3A is a view from the front, facing a patient's chest, while FIG. 3B is a view from the left of a patient, each view showing only the ICD components and the heart. Position X is disposed on the left side of the rib cage, inferior to the arm, and is designated herein as the lateral position. Position Y is a frontal position, inferior to the inframammary crease (IC) and is designated herein as the inframammary position. Finally, position Z is also a frontal position and can correspond to a conventional positioning for ICDs. This position is located superior and to the left of the heart (H) and inferior the collarbone (CB). This position Z is designated herein as the pectoral position.

Similarly, FIGS. 3A and 3B show four subcutaneous positions (A, B, C and D) for the placement of the subcutaneous electrode system 12 upon a patient's thoracic region. Position A is a parasternal placement that is positioned on the left side of the sternum (ST). Position B is an electrode placement that runs parallel to the sternum (ST), but position B is located laterally as opposed to the parasternal placement of position A. Position C is an electrode placement that is generally orthogonal to positions A and B and is positioned on a line superior to the heart (H). Finally, position D is an electrode placement that is parallel with position C, but has the electrode positioned in a line inferior to the patient's heart (H).

Figure 4:
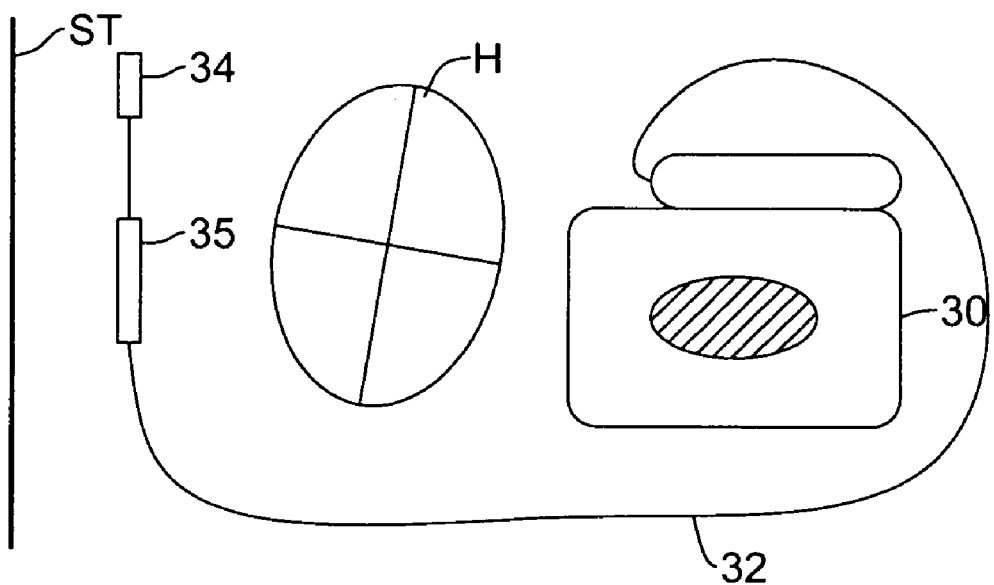
FIG. 4 illustrates a laterally placed implantable cardiac treatment system with a parasternally placed electrode.

FIG. 4 illustrates a laterally placed (X) ICD canister 30 with a parasternally placed (position A) subcutaneous electrode system along lead 32. FIG. 4 shows the lead 32 traversing subcutaneously along the ribcage and terminating in a position where the subcutaneous electrode system of the lead 32 is disposed vertically and parallel to the patient's sternum (ST). The first sensing electrode 34 is shown positioned at or near a line superior to the patient's heart (H). A coil electrode 35 is also shown, with the coil electrode 35 coupled for use as a shocking electrode, and, optionally, as an additional sensing electrode.

Figure 5:
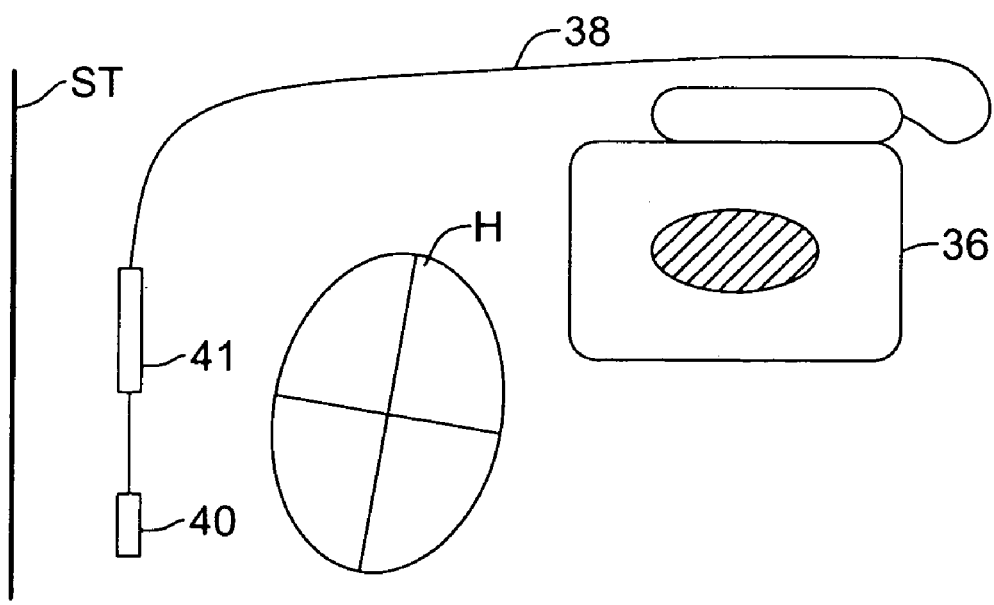
FIG. 5 illustrates a pectorally placed implantable cardiac treatment system with a parasternally placed electrode.

FIG. 5 similarly illustrates a pectorally placed (Z) ICD canister 36 with a parasternally placed (position A) subcutaneous electrode system including a lead 38. FIG. 5 also shows the lead 38 traversing subcutaneously along the ribcage and terminating such that the subcutaneous electrode system of the lead 38 is disposed vertically and parallel to the patient's sternum (ST). In contrast to the electrode placement in FIG. 3, the first sensing electrode 40 of the subcutaneous electrode system is positioned at or near a line inferior to the patient's heart (H). Again, a coil electrode 41 serving as a shocking and, if desired, sensing electrode is also illustrated.

The subcutaneous space surrounding a patient's thoracic region is inherently curvaceous. Because the canister 30, 36 (which may include a sensing electrode) and the subcutaneous electrode system on leads 32, 38 are positioned upon this region, the electrodes, canister and lead for the ICD are rarely, if ever, planar with respect to one another. Thus various vectors may be defined to intersect the heart (H), without necessarily having to place electrodes in the heart (H).

The distance separating the canister 30, 36 and the electrodes on the leads 32, 38 is dependent on the patient's anatomy. With the configurations shown in FIGS. 4 and 5, in a typical adult patient, the center of the canister 30, 36 is approximately 8 cm to approximately 19 cm away from the center of a shocking coil 35, 41 on the leads 32, 38. Children receiving devices according to the present invention may have separations between the canister and the shocking coil 35, 41 of generally no less than approximately 4 cm.

Subcutaneous embodiments of the present invention benefit from the ability to optimize the intra-electrode distance to maximize the sensing of cardiac electrical activity. Because subcutaneous embodiments of the present invention are not constrained by the location of electrodes within the system or within the patient's thorax, a subcutaneous system may use intra-electrode distances particularly chosen for optimizing far-field signal sensing, or may vary the sensing electrode pair during operation to optimize sensing.

FIG. 6A-6F depict observed electrocardiogram (EKG) signals from two small surface area electrodes having differing intra-electrode distances. In these figures, one of the two small surface area electrodes was placed in a fixed position located laterally 0.5" from the sternum, and over the patient's heart. The second of the two small surface area electrodes was positioned specific distances from the first electrode to observe and record the change in the resulting EKG.

Figure 6A:
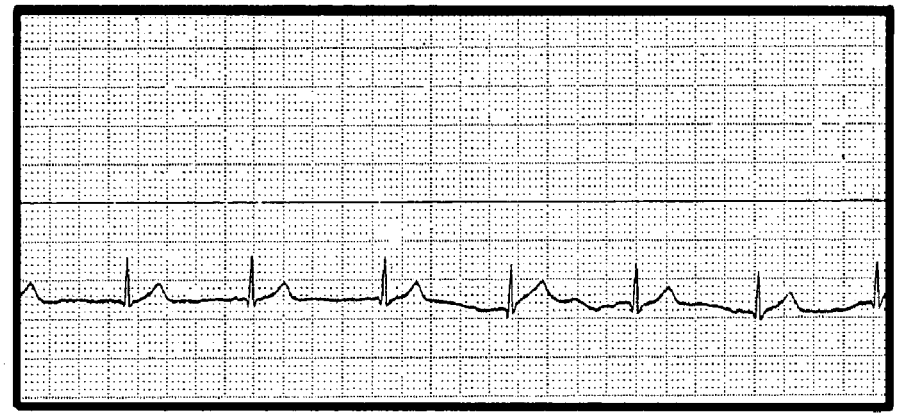
FIGS. 6A-6F depict recorded electrocardiograms from several discrete intra-electrode distances.
Figure 6B:
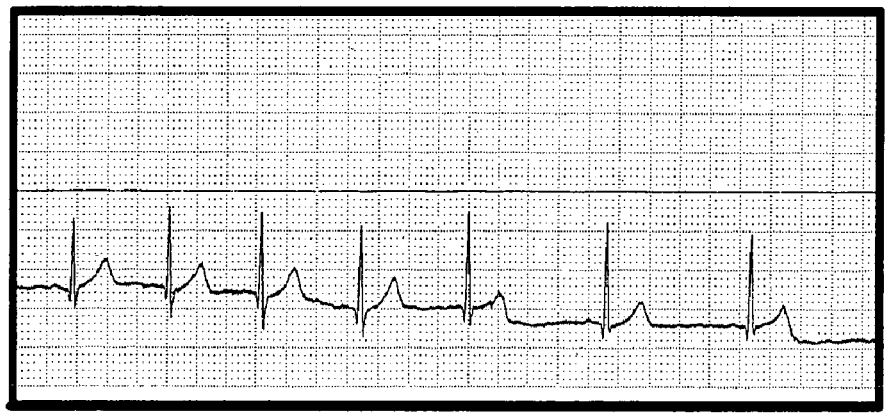
Figure 6C:
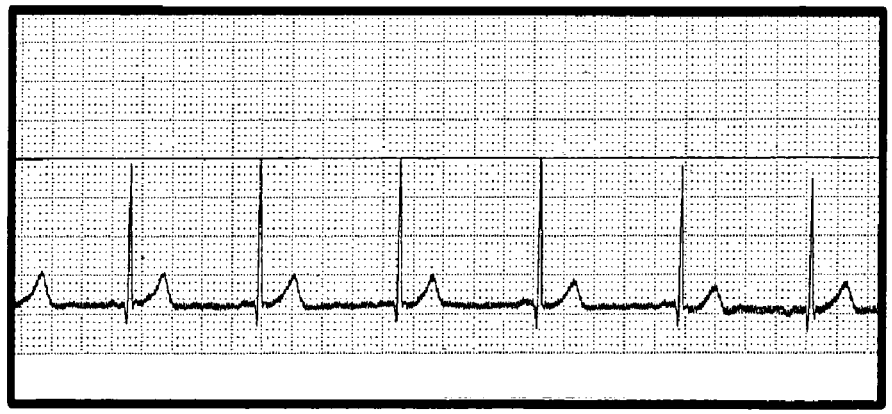
Figure 6D:
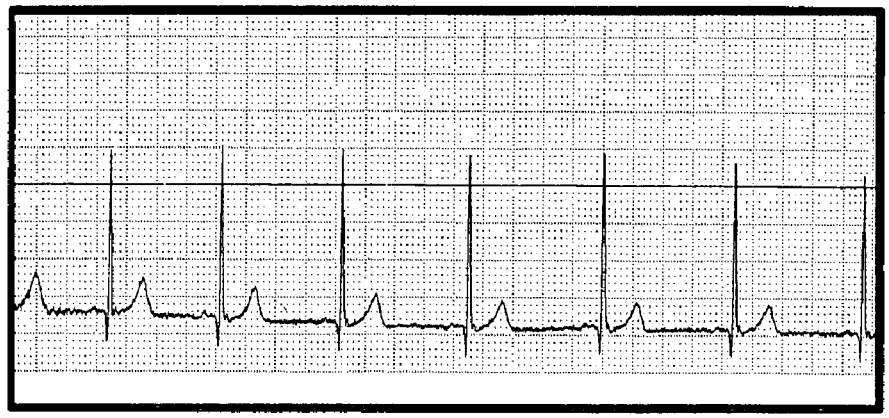
Figure 6E:
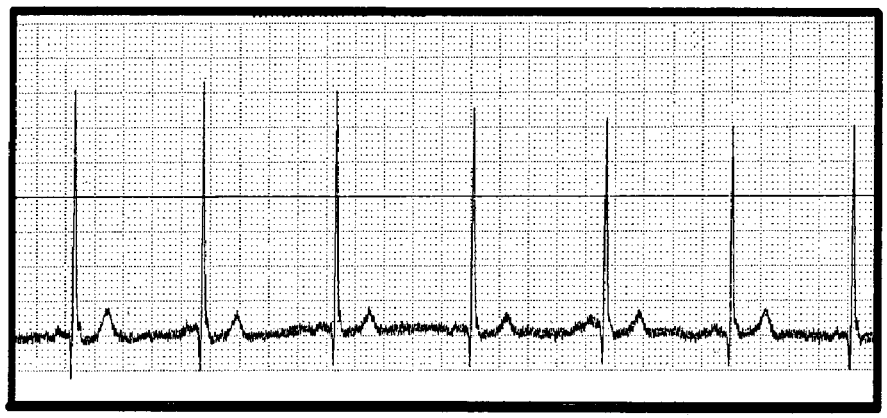
Figure 6F:

Initially, the second electrode was placed laterally 0.75" from the fixed electrode, thereby creating an intra-electrode distance of approximately 0.75". An EKG was then observed of the cardiac electrical activity. FIG. 6A represents a portion of the recorded EKG where the electrodes possessed an intra-electrode distance of approximately 0.75". Additional EKGs were recorded to measure the sensed cardiac activity after positioning the second electrode laterally approximately 1.25", 2", 2.5", 3.25" and 5.5" away from the fixed electrode position. The resulting EKGs are shown in FIGS. 6B-6F, respectively. The average observed amplitude for the QRS complex was approximately 1.0 mV in FIG. 6A, approximately 2.0 mV in FIG. 6B, approximately 4.4 mV for FIG. 6C, approximately 5.5 mV for FIG. 6D, approximately 7.8 mV for FIG. 6E and approximately 9.6 mV for FIG. 6F.

Subcutaneous embodiments of the present invention are not constrained by the location of electrodes to intravenous or intracardiac locations. As such, the subcutaneous system may use intra-electrode distances that are particularly chosen for optimizing far-field signal sensing. It is observed in FIGS. 6A-6F that increasing the intra-electrode distance results in significantly increased signal amplitudes. A 100% increase in amplitude was observed between the recorded cardiac electrical activity in FIG. 6B and FIG. 6A. A 340% increase in amplitude was observed between the recorded cardiac electrical activity in FIG. 6C and FIG. 6A. A 450% increase in amplitude was observed between the recorded cardiac electrical activity in FIG. 6D and FIG. 6A. A 680% increase in amplitude was observed between the recorded cardiac electrical activity in FIG. 6E and FIG. 6A. Finally, an 860% increase in amplitude was observed between the recorded cardiac electrical activity in FIG. 6F and FIG. 6A.

It is appreciated by those skilled in the art that it is desirable to obtain the highest signal amplitudes possible when sensing. Specifically, because detected cardiac electrical signals are processed to classify particular rhythms, the larger the cardiac electrical signal the greater the opportunity to correctly classify a rhythm. Some embodiments of the present invention provide an enhanced opportunity to correctly classify arrhythmias by using intra-electrode distances particularly chosen for optimizing far-field signal sensing.

Some embodiments of the present invention are further capable of choosing the most appropriate electrode vector to sense within a particular patient. In one embodiment, (referring to FIG. 1) after implantation, the ICD is programmed to sense between several available electrode vectors—$v_1$, $v_2$, $v_3$ and $v_4$. The ICD system then senses a series of cardiac signals using some or all of the available electrode vectors, or a preset number of available electrode vectors. In certain embodiments, the ICD system then determines the most appropriate electrode vector for continuous sensing based on which electrode vector results in the greatest signal amplitude, or performs best using some other metric such as signal-to-noise ratio (SNR). The electrode vector possessing the highest quality metric (e.g., amplitude or SNR) is then set as the default electrode vector for continuous sensing. In certain embodiments, the next alternative electrode vector is selected based on being generally orthogonal to the default electrode vector. For example, if electrode vector $v_3$, is selected as the default vector, the next alternative electrode vector may be $v_2$, an electrode vector generally orthogonal to $v_3$. In yet other embodiments the next alternative electrode vector is selected based on possessing the next highest quality metric after the default electrode vector.

Recognizing that patient anatomies vary, the present invention is not intended to be limited to purely or strictly orthogonal sensing vectors. In some embodiments, generally orthogonal sensing vectors are considered to exist when two sensing vectors create an angle such that the magnitude of the cosine of the angle is less than about 0.7. In another embodiment, the magnitude of the cosine of the angle is less than about 0.5. In a further embodiment, the magnitude of the cosine of the angle is less than about 0.3. As used herein, the phrase "the magnitude of" indicates absolute value when applied to a scalar value such as the cosine of an angle. This angular analysis is used herein because, while two vectors may define a plane, an intersection of two vectors can define a plurality of angles. Analysis in terms of cosines assures the same result regardless how the vectors are disposed with respect to one another for the purpose of determining the angles therebetween. Dealing only in first quadrant angles, the above noted values for cosines yield angles of between about 45 and 90 degrees, about 60 and 90 degrees, and about 72 and 90 degrees.

In one embodiment of the present invention, the ICD system determines the most appropriate electrode vector based on results of an operation performed on all of the sensed signals. The ICD system independently operates on all of the sensed signals received from each of the possible electrode vectors using the ICD system's detection architecture. For example, the ICD system may run all of the signals from each of the electrode vectors through a correlation waveform analysis, or a similar operation function. Specifically, the ICD system performs a correlation waveform analysis on electrode vectors $v_1$, $v_2$, $v_3$ and $v_4$ independently. The ICD system then evaluates the results from each of the independently operated-on signals. This evaluation procedure determines the electrode vectors that yield the highest quality metric for rendering a decision. Finally, the ICD system selects the electrode vector yielding the highest quality metric as the default electrode vector for continuous sensing. For example, the ICD system will select the electrode vector $v_3$ as the default electrode vector if it yields the highest quality metric from the four electrode vectors evaluated.

In certain embodiments, the ICD system paretos (prioritizing according to the hierarchy of performance) the electrode vectors. By paretoing the electrode vectors, the ICD system may utilize alternative electrode vectors, in particular the next best performing electrode vectors, when ambiguities arise in analysis of the default electrode vector.

For certain embodiments of the present invention, the evaluation of the best electrode vectors for sensing are updated periodically by the physician. A programmer responsive to the ICD system may receive transmissions from the ICD system. Amongst others, the transmissions from the programmer characterize the cardiac activity sensed by each electrode vector. The physician may then select the optimal electrode vector for the particular patient and set that chosen electrode vector as the default. The programmer may additionally enable the physician to elect alternative schemes for instances where the signal from the default electrode vector is compromised. Additionally, the programmer may select the optimal electrode vector and elect alternative schemes automatically based on the received transmissions from the ICD system.

In yet alternative embodiments, the evaluation of the best electrode vectors for sensing is updated periodically by the ICD system, whether that decision is made a priori (e.g., by signal amplitude) or ex post facto (e.g., after operating on the unprocessed signal data). For example, initially the highest quality metric (e.g., highest amplitude signal) is sensed using electrode vector $v_1$. Sometime after implantation, however, the ICD system may determine that the highest quality metric is experienced when sensing through the electrode vector $v_2$. Conversely, it may be periodically determined that the best electrode vector continues to remain with electrode vector $v_1$ during the entire life of the device.

An example of an a priori update would be one where the SNR is measured for each of several vectors over time. If a muscle artifact develops after implantation, or if a fibroid forms around one of the sensing electrodes, then the relative SNR of the several sensing vectors may change over time. If one of the sensing vectors provides a superior SNR to that of the initially chosen vector, then the later update may select a different vector.

An example of an ex post facto update would be one where a particular sensing vector is chosen for a period of time, but proves to be unsuitable for analysis, for example, due to noise artifacts. For example, if a beat validation scheme is used as explained in co-pending U.S. patent application Ser. No. 10/858,598 filed Jun. 1, 2004, entitled METHOD AND DEVICES FOR PERFORMING CARDIAC WAVEFORM APPRAISAL, now U.S. Pat. No. 7,248,921, which is incorporated herein by reference, then consistent failure to capture validated beats may indicate that the chosen vector is unsuitable. Likewise, if a template formation system relies upon captured data, then a failure to capture a template meeting chosen validity criteria may indicate that the chosen vector is unsuitable. In such cases, another sensing vector may be chosen by looking at the next best sensing vector. For example, if a first vector is chosen for sensing because it has a best amplitude of sensed vectors, supposing that first vector proves to be unsuitable for template formation, then a second vector having the second best amplitude may be chosen.

The periodicity used to evaluate the best electrode vector is preferably based on whether the sensed cardiac electrical signal is ambiguous to the ICD system's detection architecture. With respect to this invention, ambiguity concerns whether the sensed cardiac electrical signal is difficult to comprehend, understand, or classify by the ICD system's detection architecture. This process is illustrated by example in FIG. 7.

Figure 7:
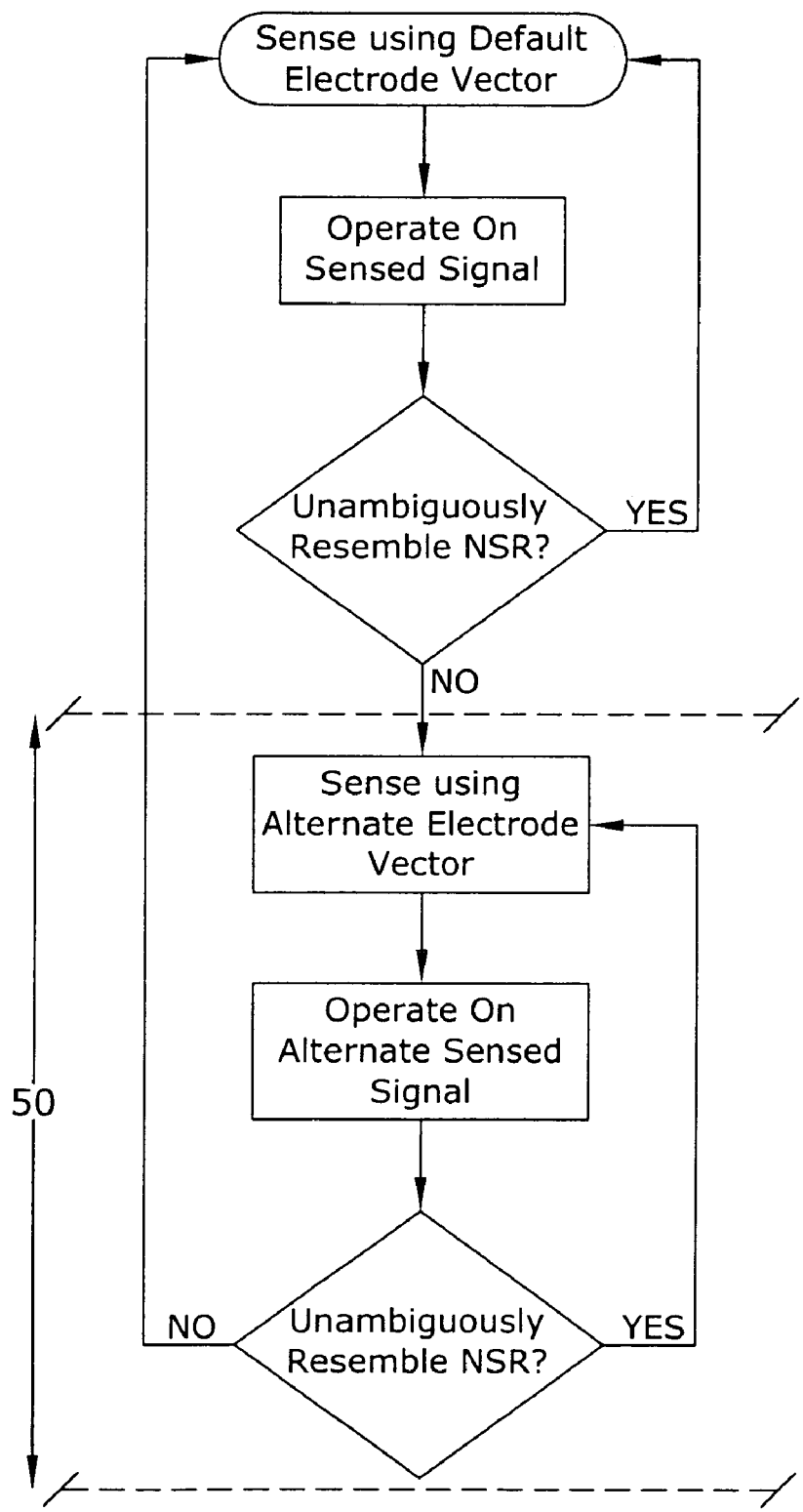
FIG. 7 shows a block diagram of the vector sensing evaluation for determining the periodicity to evaluate the best electrode vector based on observed ambiguous signals.

Referring now to FIG. 7, a cardiac electrical signal is sensed through electrode vector $v_1$. The sensed signal is then operated on by the detection architecture of the ICD system. The result of this operation is then evaluated. In certain embodiments, the ICD system will evaluate whether the operated-on signal equates unambiguously to a normal sinus rhythm. If the result of the operation unambiguously indicates a normal sinus rhythm, then the ICD system repeats the procedure and senses another cardiac electrical signal to operate upon. However, if the result of the operation is ambiguous, or the operated-on signal indicates a rhythm other than normal sinus, then the process enters a second stage 50. Some illustrative explanations of ambiguity can be found in U.S. patent application Ser. No. 10/856,084 filed May 27, 2004, entitled METHOD FOR DISCRIMINATING BETWEEN VENTRICULAR AND SUPRAVENTRICULAR ARRHYTHMIAS, which is incorporated herein by reference.

In the second stage 50, the sensing of the next cardiac electrical signal in time is performed through an alternative electrode vector. In some embodiments, the alternative electrode vector used for this sensing is one that is generally orthogonal to the electrode vector used to sense the previous signal. For example, if the previous cardiac electrical signal was sensed through electrode vector $v_1$, the next cardiac electrical signal would be sensed through electrode vector $v_2$. In alternative embodiments of the present invention, any of the remaining electrode vectors may be used to sense the next cardiac electrical signal in the second stage 50. For example, a next highest amplitude sensing vector may be chosen.

This subsequently sensed signal is then operated on by the detection architecture of the ICD system. The result of this operation is again evaluated. If the result of the operation unambiguously indicates a normal sinus rhythm from this alternative electrode vector, then the ICD system repeats the procedure and senses another cardiac signal to operate upon. In certain embodiments, subsequently sensed cardiac signals following the second stage 50 continue to be sensed through the electrode vector used for evaluation in the second stage 50. Thus in the previous example, all subsequently sensed cardiac electrical signals would be sensed using electrode vector $v_2$. However, in particular embodiments, this is only true if the result of the second stage 50 operation unambiguously indicates a normal sinus rhythm. If the result of the second stage 50 is again ambiguous, or the operated-on signal unambiguously indicates a rhythm other than normal sinus, then future sensed cardiac electrical signals may once again be processed using the default electrode vector—here being $v_1$.

In yet alternative embodiments, the next cardiac electrical signal following any second stage 50 evaluation is again initially sensed through the default electrode vector—for this example $v_1$. In this embodiment, the default electrode vector is changed only after a series of unambiguous evaluations utilizing the second stage 50 and its alternative electrode vector.

The ICD device of the present invention may also sense between multiple electrode vectors continuously and/or independently of one another. This ability allows the present invention to evaluate the same cardiac electrical signal in time from numerous vector viewpoints. Additionally, this ability permits the ICD system to evaluate the best electrode vector based on observed ambiguous signals without failing to operate and evaluate each sensed cardiac signal. Specifically, a cardiac electrical signal is sensed through an electrode vector, for example, $v_1$. The sensed signal is then operated on by the detection architecture of the ICD system. The result of this operation is then evaluated. If the result of the operation is ambiguous, or the operated-on signal unambiguously indicates a rhythm other than normal sinus, then the process enters a second stage 50.

In the second stage 50 of this embodiment, a cardiac electrical signal sensed at the same time as the sample already evaluated, but with different electrodes, is evaluated. Therefore, both the signal previously operated on and the one which is to be operated on in the second stage 50 occurred at the same time—although acquired through a different electrode vector. The sensed signal from $v_2$ is then operated on by the detection architecture of the ICD system. The result of this operation is again evaluated. If the result of the operation unambiguously indicates a normal sinus rhythm in this second electrode vector, then the ICD system repeats the procedure and senses another cardiac electrical signal in which to operate upon.

The general ability to sense between multiple sensing vectors particularly enhances specificity for detection architectures that discriminate between arrhythmias. Specifically, sensing between multiple electrode vectors enhances specificity in discriminating the origin and type of arrhythmia. In one example of the present invention, a cardiac complex representative of normal sinus rhythm (NSR) is captured from each of electrode vector $v_1$ and electrode vector $v_2$, and then stored. These are stored as NSR template 1 and NSR template 2, respectively. Because electrode vectors $v_1$ and $v_2$ are at different angles to the heart, their respective templates may differ significantly even though they may be based upon the same cardiac events.

From beat to beat, sensed complexes may be compared to their respective NSR templates. As an example, in certain vector orientations ventricular originating arrhythmias may resemble an NSR. With ICD systems that sense only one electrode vector, some ventricular arrhythmias may not be distinguishable to a detection architecture. In the present invention, however, the chances of failing to classify a particular rhythm are reduced through the use of multiple views. In particular, although a ventricular originating arrhythmia may resemble the NSR template in one view, it would be highly unlikely that a second electrode vector would also sense the same complex as resembling its NSR template.

Ventricular originating arrhythmias often exhibit a polarity flip with relation to their NSR. If this polarity flip goes undetected because of positioning in one electrode vector, a generally orthogonally positioned second electrode vector would most likely sense such a flip when compared to its NSR template. Thus, the detection algorithm would classify the uncharacteristic complex, or series of complexes, and assess the complexes as a ventricular arrhythmia.

In one embodiment, an initial analysis of the default electrode vector captured using a default electrode pair may yield an ambiguous result. For example, if a correlation waveform analysis is performed to compare a sensed signal to an NSR template, the waveform analysis may indicate that NSR is not occurring. However, it may not be clear from the initial analysis what type of arrhythmia is occurring (for example, a supraventricular arrhythmia which does not require treatment, or a ventricular arrhythmia that does require treatment). In the illustrative example, a second level of analysis may be performed using a signal captured using different electrodes to differentiate treatable and untreatable arrhythmias. The method may then return to observing only the default electrode pair.

Figure 8A:
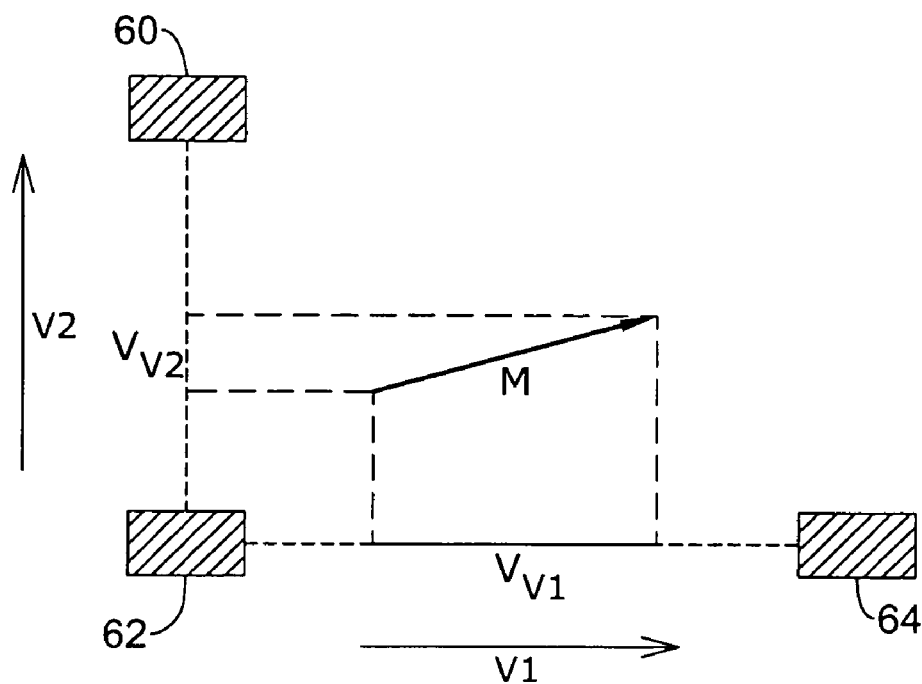
FIGS. 8A and 8B show the relationships between two electrode vectors on sensing a cardiac depolarization vector.
Figure 8B:
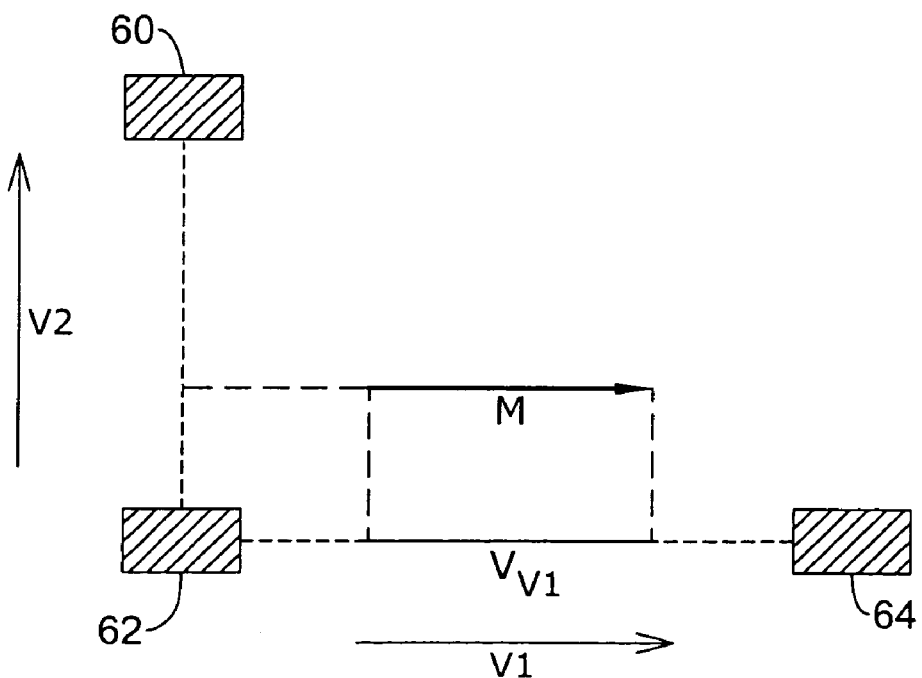

FIGS. 8A and 8B demonstrate the relationship between two electrode vectors in sensing a cardiac depolarization vector. More specifically, FIGS. 8A and 8B graphically illustrate the electrode vectors formed in the ICD system between the active canister 64 and the first sensing ring 62, and the first sensing ring 62 and the second sensing ring 60. These vectors are labeled, respectively, $v_1$ and $v_2$. FIGS. 8A and 8B further illustrate a cardiac depolarization vector M. The cardiac depolarization vector M cannot be completely described by measuring only one of the two electrode vectors shown in FIGS. 8A and 8B. More information about the cardiac depolarization vector M can be acquired using two electrode vectors. Thus, the resulting ECG derived from three or more electrodes will more accurately define a depolarization vector M, or a fraction thereof.

For the cardiac depolarization vector M, the voltage induced in the direction of electrode vector $v_1$ is given by the component of M in the direction of $v_1$. In vector algebra, this can be denoted by the dot product $$\upsilon_{v1} = M \cdot v_1$$

where $\upsilon_{v1}$ is the scalar voltage measured in the direction of electrode vector $v_1$. FIGS. 8A and 8B further depict an electrode vector $v_2$ oriented in space. The effect of the cardiac depolarization vector M as it relates to electrode vector $v_2$ differs, however, between FIGS. 8A and 8B.

FIG. 8A illustrates a cardiac depolarization vector M that includes components in both vector directions, and so is sensed and measured with scalar voltages along both electrode vectors. The cardiac depolarization vector M in FIG. 8A is oriented in space such that both electrode vectors $v_1$ and $v_2$ sense scalar voltages $\upsilon_{v1}$ and $\upsilon_{v2}$, respectively. Although the scalar voltage $\upsilon_{v1}$ predominates, the scalar voltage $\upsilon_{v2}$ is sensed and can be used for discriminating differences in the magnitude and the direction of the cardiac depolarization vector M.

In contrast, the electrode vector $v_2$ in FIG. 8B is oriented orthogonally to the cardiac depolarization vector M. In this embodiment, the component of M along the direction of vector electrode $v_2$ is zero because the $v_2$ electrode vector senses no voltage as a result of the cardiac depolarization vector; no voltage is induced in the direction of $v_2$. In contrast, the scalar voltage along $v_1$ parallels the depolarization vector M and fully captures M.

With the ability to ascertain the cardiac depolarization vector M, FIGS. 8A and 8B further depict how the present invention may be utilized to enhance a particular attribute of the sensed signal. For example, the present invention may be utilized to enhance the signal-to-noise ratio (SNR) for an ICD system. In illustration, suppose that most patients demonstrate a cardiac depolarization vector M similar to that depicted in FIG. 8A. For these patients, sensing along electrode vector v, alone would result in a sufficiently high SNR to sense and detect most arrhythmias, while vector $v_2$ provides information that may be relevant for sensing if analysis of $v_1$ contains some ambiguity.

There may be patients, however, who exhibit a cardiac depolarization vector M similar to the one depicted in FIG.

8B. These patients could exhibit a cardiac depolarization vector M at the time of implant, or after developing a pathology that changes the cardiac depolarization vector M over time to represent the one depicted in FIG. 8B. For these patients, sensing along electrode vector $v_2$ alone would result in an extremely low SNR. Furthermore, the ICD system may not be able to detect certain arrhythmic events if this were the only sensing vector the ICD system possessed. However, knowledge that $v_2$ has such a low magnitude indicates greater directional information than just analyzing $v_1$.

As described above, sensing sensitivity depends on the orientation of the cardiac depolarization vector M with respect to the orientation of the sensing electrodes.

The operational circuitry used in the implantable medical devices of the present invention may be configured to include such controllers, microcontrollers, logic devices, memory, and the like, as selected, needed, or desired for performing the steps for which each is configured.

In addition to uses in an ICD system, the present invention is also applicable to pacing systems. For example, in a pacing system a number of electrodes may be disposed to define several sensing vectors, and the present invention may guide the selection of and periodic updating of sensing vectors.

In one illustrative example, the present invention is embodied in an implantable cardiac treatment system comprising an implantable canister housing operational circuitry and a plurality of electrodes electrically coupled to the operational circuitry wherein the operational circuitry is configured and coupled to the electrodes to define at least a first implanted electrode pair and a second implanted electrode pair. The operational circuitry may be configured to perform the steps of capturing a first signal from the first implanted electrode pair, constructing a first template using the first signal, capturing a second signal from the second implanted electrode pair, constructing a second template using the second signal, and capturing a signal using the first and second electrode pairs and using the first and second templates to determine whether a treatable cardiac condition exists.

Numerous characteristics and advantages of the invention covered by this document have been set forth in the foregoing description. It will be understood, however, that this disclosure is, in many aspects, only illustrative. Changes may be made in details, particularly in matters of shape, size and arrangement of parts without exceeding the scope of the invention. The invention's scope is defined, of course, in the language in which the claims are expressed.

What is claimed is:

1. An implantable electrical cardiac treatment device comprising:
    first, second, and third electrodes, the second electrode provided at a first distance from the first electrode along a lead assembly, the third electrode provided at a second distance from the first electrode along a lead assembly; and
    operational circuitry electrically coupled to the first, second and third electrodes such that sensing can be performed using any pair chosen therefrom;
    wherein the operational circuitry is adapted to perform the following steps:
    observe a signal metric between at least two of the following sensor pairs: first-second, first-third, and second-third; and
    select a default sensor pair for use in cardiac signal analysis by determining which pair performs the best as measured by the signal metric;
    and further wherein the operational circuitry is adapted to perform the following data analysis:
    analyzing a first signal captured from the default electrode pair and determining whether:
    a normal sinus rhythm has been sensed;
    an arrhythmia has been sensed; or
    ambiguity is present; and
    if ambiguity is present, selecting a second electrode pair using the signal metric and analyzing a second signal captured from the second electrode pair.

2. The device of claim 1, wherein the first electrode is a housing electrode.

3. The device of claim 1, wherein the operational circuitry is adapted to perform the following steps: perform data analysis of sensed cardiac signals; determine whether the default sensor pair is providing a suitable signal for cardiac signal analysis; and if not, selecting a different sensor pair for use in cardiac signal analysis.

4. The device of claim 1, wherein the operational circuitry is adapted to provide an output signal using one of the electrode pairs.

5. The device of claim 1, further comprising a fourth electrode disposed as part of the lead assembly, the fourth electrode being a coil electrode, wherein the operational circuitry is configured to provide an output signal using the first electrode and the fourth electrode.

6. The device of claim 5, wherein the operational circuitry is adapted to consider electrode pairs including the fourth electrode and any of the first, second and third electrodes when performing the steps of observing a signal metric and selecting a default electrode pair.

7. The device of claim 1, wherein the operational circuitry is adapted such that the second signal temporally corresponds to at least part of the first signal.

8. A method of cardiac signal analysis comprising:
    implanting an implantable electrical cardiac treatment device and associated lead assembly into a patient such that operational circuitry housed in the device is coupled to first, second, and third electrodes;
    observing a signal metric between two pairs of electrodes chosen from the first, second and third electrodes;
    identifying a default electrode pair based upon observation of the signal metric; and
    using the default electrode pair for sensing of cardiac signals;
    analyzing a first signal captured from the default electrode pair and determining whether:
    a normal sinus rhythm has been sensed;
    an arrhythmia has been sensed; or
    ambiguity is present; and
    if ambiguity is present, selecting a second electrode pair and analyzing a second signal captured from the second electrode pair.

9. The method of claim 8, further comprising: determining whether the default electrode pair provides a suitable signal for cardiac signal analysis; and if not, using a different electrode pair for sensing cardiac signals.

10. The method of claim 8, wherein one of the electrodes is provided such that it is on a housing electrode.

11. The method of claim 10, further comprising generating a cardiac stimulus using an electrode pair including the housing electrode.

12. The method of claim 8, further comprising:
    performing data analysis of sensed cardiac signals;
    determining whether the default sensor pair provides a suitable signal for cardiac signal analysis; and, if not, using a different sensor pair in cardiac signal analysis.

13. The method of claim 8, wherein the step of selecting a second electrode pair includes using the signal metric and identifying the second electrode pair as a pair of electrodes achieving a highest signal metric outside of the first electrode pair.

14. The method of claim 8, wherein the second signal temporally corresponds to at least part of the first signal.

15. The method of claim 8, wherein the step of implanting an implantable electrical cardiac treatment device and associated lead assembly into a patient includes disposing the lead electrode assembly such that the first, second, and third electrodes define at least two generally orthogonal sensing vectors.

16. The method of claim 15, wherein the lead electrode assembly is disposed such that two sensing vectors create at an angle such that the magnitude of the cosine of the angle is less than about 0.7.

17. The method of claim 16, wherein the magnitude of the cosine of the angle is less than about 0.5.

18. The method of claim 17, wherein the magnitude of the cosine of the angle is less than about 0.3.

19. The method of claim 8 wherein the step of selecting a second electrode pair includes identifying a second electrode pair defining a vector therebetween that is generally orthogonal to a vector defined by the first electrode pair.

20. The method of claim 8 wherein the step of implanting is performed such that the canister and lead assembly are subcutaneously implanted with no portion thereof inserted into a chamber of the patient's heart, the patient's heart muscle, or the patient's vasculature.

21. A method of operating an implantable electrical cardiac treatment device having operational circuitry for performing cardiac performance evaluation and treatment, the method comprising:
  coupling first, second, and third implanted electrodes to the operational circuitry;
  observing a sensing metric for selected pairs of the implanted electrodes;
  identifying a default electrode pair for use in evaluation of cardiac signals;
  identifying a second best electrode pair for use in evaluation of cardiac signals;
  analyzing a first signal captured using the default electrode pair and determining whether;
  the first signal indicates a normal sinus rhythm;
  the first signal indicates a particular arrhythmia; or
  the first signal indicates ambiguity; and
  if the first signal indicates ambiguity, analyzing a second signal captured using the second best electrode pair.

22. The method of claim 21 wherein the steps of analyzing a first signal and analyzing a second signal if the first signal indicates ambiguity comprise analyzing cardiac signal data captured at the same time for each of the first and second signals.

* * * * *